(12) United States Patent
Lin

(10) Patent No.: US 10,188,543 B2
(45) Date of Patent: Jan. 29, 2019

(54) FOLDING MENSTRUAL CUP

(71) Applicant: Guangzhou Tianyuan Silicone Machine Technology Co., Ltd, Guangdong (CN)

(72) Inventor: Yecheng Lin, Guangdong (CN)

(73) Assignee: Guangzhou Tianyuan Silicone Machine Technology Co., Ltd., Guangdong (CN)

( * ) Notice: Subject to any disclaimer, the term of this patent is extended or adjusted under 35 U.S.C. 154(b) by 184 days.

(21) Appl. No.: 15/306,964

(22) PCT Filed: Oct. 10, 2015

(86) PCT No.: PCT/CN2015/091594
§ 371 (c)(1),
(2) Date: Oct. 26, 2016

(87) PCT Pub. No.: WO2017/031813
PCT Pub. Date: Mar. 2, 2017

(65) Prior Publication Data
US 2017/0189222 A1    Jul. 6, 2017

(30) Foreign Application Priority Data

Aug. 25, 2015  (CN) .......................... 2015 1 0531933

(51) Int. Cl.
*A61F 5/44*    (2006.01)
*A61F 5/455*   (2006.01)

(52) U.S. Cl.
CPC .......... *A61F 5/4405* (2013.01); *A61F 5/4553* (2013.01)

(58) Field of Classification Search
CPC .................. A61F 5/451–5/4556; A61F 5/4405
See application file for complete search history.

(56) References Cited

U.S. PATENT DOCUMENTS

| | | | | |
|---|---|---|---|---|
| 2,613,670 A | * | 10/1952 | Sokolik ................ | A61F 5/4553 128/834 |
| 3,845,766 A | * | 11/1974 | Zoller .................. | A61F 5/4553 604/330 |
| 4,381,771 A | * | 5/1983 | Gabbay ................. | A61F 6/08 128/836 |

(Continued)

OTHER PUBLICATIONS

"Silica gel," Britannica Online Encyclopedia, printed Jun. 22, 2018.*

(Continued)

*Primary Examiner* — Susan S Su
(74) *Attorney, Agent, or Firm* — Head, Johnson, Kachigian & Wilkinson, PC

(57) ABSTRACT

A folding menstrual cup comprising an outer cup body with a top accommodating cavity formed therein and a round opening provided on the top thereof and the bottom thereof being connected with a flow guiding pipe via a folding part at the side opposite to the opening; a flow guiding pipe providing with a pipe orifice communicating with the top accommodating cavity and a valve controlling communication to the pipe orifice; and a folding part being capable of protruding upward and enabling the top end of the flow guiding pipe to extend into the top accommodating cavity along with the folding part, and capable of straightening downward thereby a bottom accommodating cavity is formed inside the folding part. When in use, the folding part extends into the top accommodating cavity of the outer cup body and is placed in a body.

8 Claims, 2 Drawing Sheets

(56) References Cited

U.S. PATENT DOCUMENTS

| | | | | |
|---|---|---|---|---|
| 4,531,245 A * | 7/1985 | Lowd | A47K 11/00 | 141/337 |
| 4,713,066 A * | 12/1987 | Komis | A61F 5/453 | 604/349 |
| 4,810,247 A * | 3/1989 | Glassman | A61F 5/453 | 604/171 |
| 5,243,712 A * | 9/1993 | Cross | A61F 5/4556 | 4/144.2 |
| 5,295,984 A * | 3/1994 | Contente | A61K 9/0036 | 604/317 |
| 5,370,637 A * | 12/1994 | Brodeur | A61F 5/4556 | 4/144.3 |
| 5,827,248 A * | 10/1998 | Crawford | A61F 5/4553 | 604/328 |
| 6,168,609 B1 * | 1/2001 | Kamen | A61F 5/4553 | 600/573 |
| 6,902,146 B1 * | 6/2005 | Elliott | A61F 5/4405 | 251/351 |
| 8,684,984 B2 * | 4/2014 | Bjerregaard | A61F 5/453 | 206/364 |
| 2001/0018577 A1 * | 8/2001 | Fitzpatrick | A61F 5/4553 | 604/328 |
| 2007/0191795 A1 * | 8/2007 | Di Croce | A61F 5/4556 | 604/347 |
| 2008/0077097 A1 * | 3/2008 | Chambers | A61F 5/4553 | 604/330 |
| 2008/0200888 A1 * | 8/2008 | Gooch | A61F 5/4553 | 604/330 |
| 2010/0016821 A1 * | 1/2010 | Bjerregaard | A61F 5/453 | 604/349 |
| 2011/0190579 A1 * | 8/2011 | Ziarno | A61B 1/00016 | 600/109 |
| 2015/0027452 A1 * | 1/2015 | Ehlers | A61B 5/1171 | 128/884 |
| 2016/0354230 A1 * | 12/2016 | Abuhaikal | A61F 5/4556 | |
| 2017/0049609 A1 * | 2/2017 | Conti | A61F 6/12 | |
| 2017/0360594 A1 * | 12/2017 | Park | A61F 2/0009 | |

OTHER PUBLICATIONS

"Silicone," Britannica Online Encyclopedia, printed Jun. 22, 2018.*

* cited by examiner

FOLDING MENSTRUAL CUP

FIELD OF THE INVENTION

The present invention relates to the field of a physiological product, and particularly relates to a folding menstrual cup.

BACKGROUND OF THE INVENTION

Females may suffer from lower abdomen pains and a falling distention feeling together with waist soreness and other discomforts before and after the menstrual period or during the menstrual period, and these symptoms seriously influence the living quality. A menstrual ball is a feminine physiological product, a female usually uses a sanitary napkin for nursing when the physiological cycle arrives, but the sanitary napkin commonly has some defects in the using process. For example, the sanitary napkin is a product for external use, which cannot relieve the lower abdomen pains and the falling distention feeling which occur in the menstrual period and which may cause a leakage due to an improper placement in use or poor liquid absorbing capacity of the sanitary napkin. Moreover, when the female walks or does some exercises, friction is generated between side walls of the sanitary napkin and both legs, which may makes the user uncomfortable. Since the sanitary napkin is a product for external use and adsorbing liquid, the female cannot take part in underwater activities, e.g., swimming and the like, when she is using a sanitary napkin. In order to solve various problems above, currently, reusable menstrual cups are commercially available, the existing menstrual cups are all of a fixed shape structure, a closed effect is generated after the menstrual cup is placed into the vagina of a female, and during the menstrual period, a menstrual cup body structure is used for containing menstrual blood. However, when the menstrual blood is discharged out of the body, air in the menstrual cup cannot be exhausted, thus the female will have an abdominal distention feeling when using the menstrual cup.

SUMMARY OF THE INVENTION

In order to solve the mentioned problems, the present invention provides a folding menstrual cup which avoids pollution in the processes of frequently taking out from and placing back into a human body, and which is more comfortable in use.

For solving the mentioned technical problems, the present invention employs a technical solution by providing a folding menstrual cup includes:

an outer cup body, wherein a top accommodating cavity is formed inside the outer cup body, a round opening is provided at the top of the outer cup body, at a side opposite to the opening, the bottom of the outer cup body is connected to the flow guiding pipe via a folding part;

a flow guiding pipe providing with a pipe orifice communicating with the top accommodating cavity of the outer cup body, a valve controlling communication to the pipe orifice is arranged on the flow guiding pipe; and a folding part being capable of protruding upward and enabling the top end of the flow guiding pipe to extend into the top accommodating cavity of the outer cup body along with the folding part; wherein the folding part is capable of straightening downward and a bottom accommodating cavity is formed inside the folding part.

Furthermore, as an improvement of the technical solution of the present invention, the folding part comprises a cup body end connected to the bottom edge of the outer cup body, and a catheter end connected to a top pipe orifice of the flow guiding pipe, and the aperture of the cup body end is greater than that of the catheter end.

Furthermore, as an improvement of the technical solution of the present invention, a plurality of ring-shaped bulges arranged closely one another are formed along the inner wall of the folding part, and a fold deformable by folding is formed between each two adjacent ring-shaped bulges.

Furthermore, as an improvement of the technical solution of the present invention, each of the ring-shaped bulges is provided with an arc surface which is raised toward the inside of the folding part.

Furthermore, as an improvement of the technical solution of the present invention, convex rings are provided respectively outside the top edge of the outer cup body and outside the bottom edge of the outer cup body.

Furthermore, as an improvement of the technical solution of the present invention, the valve comprises two flexible valve plates which extend out of a side wall of the pipe orifice in a directly-facing manner, and the two flexible valve plates are closely abutted.

Furthermore, as an improvement of the technical solution of the present invention, bosses which are bulged upward and are closely abutted are respectively formed at the tops of the two flexible valve plates, the abutting face of each flexible valve plate is a plane, and the outer side surfaces of the bosses are inclined planes which are inclined toward the abutting face.

Furthermore, as an improvement of the technical solution of the present invention, tactile bumps are arranged, outside to the valve position, on the outer wall of the flow guiding pipe.

Furthermore, as an improvement of the technical solution of the present invention, the outer cup body, the flow guiding pipe, the folding part and the valve are integrally formed into a silica gel product.

The present invention is advantageous by offering several technical effects: the folding menstrual cup includes the outer cup body, the folding part and the flow guiding pipe; the folding part can protrude upward and extend into the top accommodating cavity of the outer cup body, or can be straightened downward and form the bottom accommodating cavity below the top accommodating cavity; during the use of the folding menstrual cup, the folding part extends into the top accommodating cavity of the outer cup body and is placed into the body, a certain pressure is generated in the body when menstrual blood of a female is discharged, the folding part can be slowly expanded downward (outward the top accommodating cavity) under the action of a certain pressure, and finally, the bottom accommodating cavity is formed; the bottom accommodating cavity and the top accommodating cavity are combined to form a menstrual cup with a larger accommodating cavity, so that all the menstrual blood discharged out of the body can be contained in the menstrual cup, and the female does not have the feeling of abdominal distention. The present invention provides the above technical solution of a folding menstrual cup which avoids pollution in the processes of frequently taking out from and placing back into a human body, and which is more comfortable in use.

BRIEF DESCRIPTION OF DRAWINGS

The present invention is further illustrated below in combination with accompanying drawings.

DETAILED DESCRIPTION OF THE EMBODIMENTS

Figure 1:
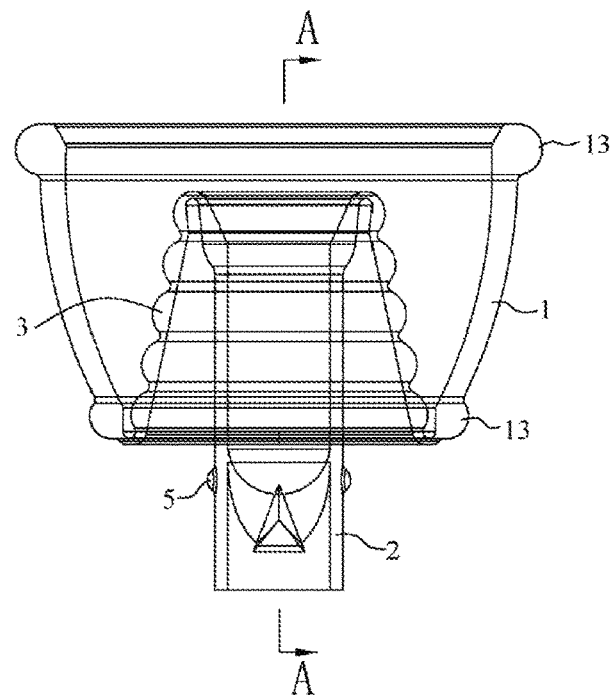
FIG. 1 is a structural schematic diagram when the top end of a flow guiding pipe extends into a top accommodating cavity of an outer cup body along with a folding part.
Figure 2:
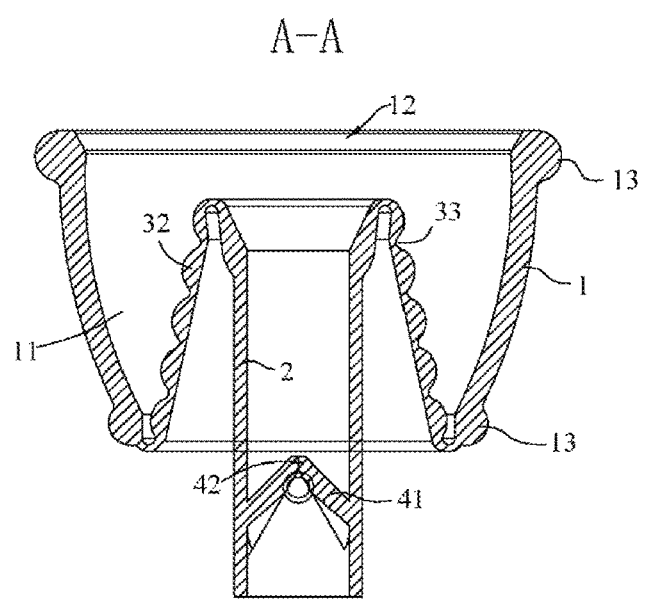
FIG. 2 is a sectional view along a line A-A in FIG. 1.
Figure 3:
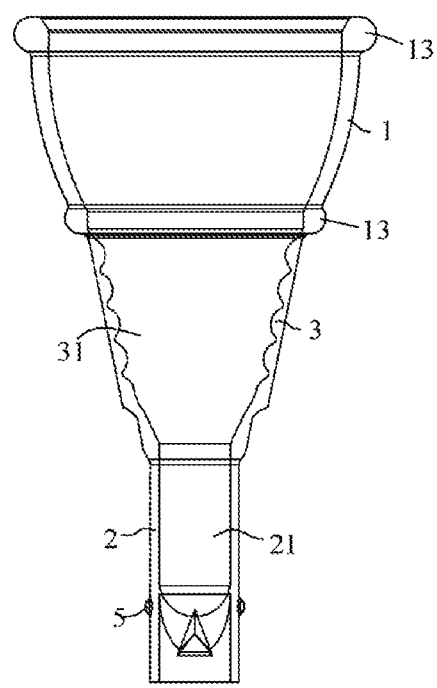
FIG. 3 is a structural schematic diagram when a folding part according to the present invention is straightened downward.

With reference to FIG. 1 to FIG. 3, specific structures of preferable embodiments of the present invention are shown. Structural characteristics of each component of the present invention will be illustrated in details in the following, and when directions (up, down, left, right, front and back) are described, the structure shown in the FIG. 1 is described as reference, but the actual direction in use of the present invention is not limited thereto.

The present invention provides a folding menstrual cup which includes an outer cup body 1, a flow guiding pipe 2 and a folding part 3. A top accommodating cavity 11 is formed inside the outer cup body 1. A round opening 12 is provided at the top of the outer cup body 1. At a side opposite to the round opening 12, the bottom of the outer cup body 1 is connected to the flow guiding pipe 2 via the folding part 3. The flow guiding pipe 2 is provided with a pipe orifice 21 communicating with the top accommodating cavity 11 of the outer cup body 1. A valve capable of controlling communication to the pipe orifice 21 is arranged on the flow guiding pipe 2. The folding part 3 can protrude upward, and enables the top end of the flow guiding pipe 2 to extend into the top accommodating cavity 11 of the outer cup body 1 along with the folding part 3. Further, the folding part 3 can be straightened downward, and a bottom accommodating cavity 31 is formed inside the folding part 3. The outer cup body 1, the flow guiding pipe 2, the folding part 3 and the valve can be integrally formed by silica gel through a mould.

The folding part 3 includes a cup body end connected to the bottom edge of the outer cup body 1 and a catheter end connected to a top pipe orifice of the flow guiding pipe, and the aperture of the cup body end is greater than that of the catheter end. A plurality of closely arranged ring-shaped bulges 32 are formed along the inner wall of the folding part 3, and each of the ring-shaped bulges 32 is provided with an arc surface which is raised toward the inside of the folding part 3. A fold 33 deformable by folding is formed between each two adjacent ring-shaped bulges 32.

According to the present invention, the folding menstrual cup includes the outer cup body 1, the folding part 3 and the flow guiding pipe 2. The folding part 3 can protrude upward and extend into the top accommodating cavity 11 of the outer cup body 1, or can be straightened downward and form the bottom accommodating cavity 31 below the top accommodating cavity 11. When using the folding menstrual cup, the folding part 3 extends into the top accommodating cavity 11 of the outer cup body 1 and is placed in the body, a certain pressure is generated in the body when menstrual blood of a female is discharged, the folding part 3 can be slowly expanded downward (outward the top accommodating cavity) under the action of the certain pressure, and finally, the bottom accommodating cavity 31 is formed. The bottom accommodating cavity 31 and the top accommodating cavity 11 are combined to form a menstrual cup with a larger accommodating cavity, so that all the menstrual blood discharged out of the body can be placed in the menstrual cup, and the female does not have a feeling of abdominal distention. According to the present invention, by the above technical solution, not only the pollution generated in the process of frequently taking the menstrual cup out of the human body and placing back the menstrual cup in the human body is avoided, but also higher comfortableness is achieved.

Convex rings 13 are arranged outside both the top edge of the outer cup body 1 and the bottom edge of the outer cup body 1. The convex rings 13 have an effect of improving a tensioning force of the round opening, and meanwhile, the convex ring 13 at the top of the outer cup body 1 can improve anastomotic force of the opening and the cervix uteri so as to prevent a leakage.

The valve includes two flexible valve plates 41 which extend out of the side wall of the pipe orifice 21 in a directly-facing manner (i.e. facing with each other), and the two flexible valve plates 41 are closely abutted. Bosses 42 which are bulged upward and are closely abutted are formed at the tops of the two flexible valve plates 41, and the bosses 42 can generate a self-closing force under the pressure of liquid so as to acquire a better sealing. The abutting face of each of the two flexible valve plates 41 is a plane, the outer side surfaces of the bosses 42 are inclined planes which are inclined toward the abutting face. Tactile bumps 5 are arranged, outside the valve position, on the outer wall of the flow guiding pipe 3. The valve works to prevent the liquid in the menstrual cup from flowing out, and when the liquid inside the menstrual cup needs to be discharged, a user only needs to cooperate with the tactile bumps 5 and forcedly squeezes the flexible valve plates 41 to enable the flexible valve plates 41 to be deformed, so that the menstrual cup can be opened to enable the liquid to flow out. The valve is designed in a structure with two inwardly convex flexible valve plates 41, wherein the two flexible valve plates 41 are tightly closed together in a normal state so as to effectively prevent liquid from flowing there through, however in a state that a large amount of liquid is stored in the menstrual cup and the menstrual cup is oppressed in a human body, a certain pressure will be formed, the pressure will in turn acts on the flexible valve plates 41 making the flexible valve plates 41 close more tightly, thereby effectively preventing a leakage under such a certain pressure.

Certainly, the scope of the present invention is not limited to the above embodiments, those skilled in the art also can make equivalent modifications or substitutions without departure from the spirit of the present invention, and those equivalent modifications or substitutions shall fall within the scope defined by the claims of the present application.

The invention claimed is:

1. A folding menstrual cup comprising:
   an outer cup body with a top and a bottom, wherein a top accommodating cavity is formed inside the outer cup body and a round opening is provided at the top of the outer cup body; at a side opposite to the opening, the bottom of the outer cup body is connected to a flow guiding pipe via a folding part;
   the flow guiding pipe with a pipe orifice in communication with the top accommodating cavity of the outer cup body, where a valve controlling communication to the pipe orifice is arranged on the flow guiding pipe; and
   the folding part being capable of protruding upward and enabling the top end of the flow guiding pipe to extend into the top accommodating cavity of the outer cup body along with the folding part; wherein the folding part is capable of straightening downward and a bottom accommodating cavity is formed inside the folding part.

2. The folding menstrual cup according to claim 1, wherein the folding part comprises a cup body end connected to the bottom edge of the outer cup body, and a catheter end connected to a top pipe orifice of the flow guiding pipe, and the aperture of the cup body end is greater than that of the catheter end.

3. The folding menstrual cup according to claim 1, wherein a plurality of ring-shaped bulges arranged closely one another are formed along an inner wall of the folding part, and a fold deformable by folding is formed between each two adjacent ring-shaped bulges.

4. The folding menstrual cup according to claim 3, wherein each of the ring-shaped bulges is provided with an arc surface which is raised toward the inside of the folding part.

5. The folding menstrual cup according to claim 1, wherein convex rings are provided respectively outside the top edge of the outer cup body and outside the bottom edge of the outer cup body.

6. The folding menstrual cup according to claim 1, wherein the valve comprises two flexible valve plates which extend out of a side wall of the pipe orifice in a directly-facing manner, and the two flexible valve plates are closely abutted.

7. The folding menstrual cup according to claim 6, wherein bosses which are bulged upward and are closely abutted are respectively formed at the tops of the two flexible valve plates, the abutting face of each flexible valve plate is a plane, and the outer side surfaces of the bosses are inclined planes which are inclined toward the abutting face.

8. The folding menstrual cup according to claim 1, wherein tactile bumps are arranged, outside to the valve position, on the outer wall of the flow guiding pipe.

* * * * *